US009037295B2

(12) United States Patent
Hodgson et al.

(10) Patent No.: US 9,037,295 B2
(45) Date of Patent: May 19, 2015

(54) DYNAMIC PHYSICAL CONSTRAINT FOR HARD SURFACE EMULATION

(75) Inventors: Antony Hodgson, Vancouver (CA); Christopher Plaskos, New York, NY (US); Nikolai Hungr, Grenoble (FR)

(73) Assignee: Perception Raisonnement Action en Medecine, La Tronche (FR)

(*) Notice: Subject to any disclaimer, the term of this patent is extended or adjusted under 35 U.S.C. 154(b) by 938 days.

(21) Appl. No.: 12/399,714

(22) Filed: Mar. 6, 2009

(65) Prior Publication Data

US 2009/0228145 A1    Sep. 10, 2009

Related U.S. Application Data

(60) Provisional application No. 61/064,486, filed on Mar. 7, 2008.

(51) Int. Cl.
*B25J 19/06* (2006.01)
*A61B 19/00* (2006.01)
*A61B 17/17* (2006.01)

(52) U.S. Cl.
CPC ............ *A61B 19/30* (2013.01); *A61B 2019/304* (2013.01); *A61B 17/1742* (2013.01);
(Continued)

(58) Field of Classification Search
CPC ............ A61B 19/30; A61B 2019/305; A61B 17/1742; A61B 17/1757; A61B 17/1764; A61B 19/2203; A61B 19/5244; A61B 2019/2292; A61B 2019/303; A61B 2019/304; A61B 19/22; A61B 19/2207; A61B 19/2211; A61B 19/2215; A61B 19/2219; A61B 19/223; B25J 9/101; B25J 9/0048; B25J 9/126; B25J 9/1615; B25J 9/046; G05G 5/04; G05G 5/00; G05G 2700/00; G05G 2700/02; G05G 2700/04; G05G 2700/06; G05G 2700/10

USPC ............ 700/257, 258, 261; 901/2, 9, 14, 15, 901/27–29; 318/568.11, 568.16, 568.17, 318/568.2, 568.21, 568.22
See application file for complete search history.

(56) References Cited

U.S. PATENT DOCUMENTS 5,529,159 A    6/1996  Troccaz
5,704,253 A    1/1998  Book et al.
(Continued)

FOREIGN PATENT DOCUMENTS

WO    WO2006106419           10/2006
WO    WO 2006106419 A2  *  10/2006
WO        2007045810 A2        4/2007

OTHER PUBLICATIONS

Hungr, Nikolai, Haptic Emulation of Hard Surfaces With Applications to Orthopaedic Surgery, A Thesis Submitted in Partial Fulfilment of the Requirements for the Degree of Master of Applied Science, 2003.
(Continued)

*Primary Examiner* — Jerrah Edwards
(74) *Attorney, Agent, or Firm* — Kim Winston LLP

(57) ABSTRACT

A method and apparatus for haptic hard surface emulation using a dynamic physical constraint are provided. The movement and position of the dynamic physical constraint is actively controlled in order to emulate a hard surface. The dynamic physical constraint may be controlled by a computer. In another aspect of the invention, the dynamic physical constraint limits the motion of a manipulator joint in space. The position at any time of the dynamic physical constraint is dependent on the position in space of the manipulator's end effector.

15 Claims, 8 Drawing Sheets

(52) U.S. Cl.
CPC ......... *A61B17/1757* (2013.01); *A61B 17/1764* (2013.01); *A61B 19/2203* (2013.01); *A61B 19/5244* (2013.01); *A61B 2019/2292* (2013.01); *A61B 2019/303* (2013.01)

(56) References Cited

U.S. PATENT DOCUMENTS

| | | | |
|---|---|---|---|
| 5,952,796 | A | 9/1999 | Colgate et al. |
| 6,228,089 | B1 * | 5/2001 | Wahrburg .................. 606/86 R |
| 6,757,582 | B2 | 6/2004 | Brisson et al. |
| 6,792,398 | B1 * | 9/2004 | Handley et al. .................. 703/2 |
| 2004/0128026 | A1 | 7/2004 | Harris et al. |
| 2005/0166413 | A1 * | 8/2005 | Crampton ...................... 33/503 |
| 2005/0273198 | A1 * | 12/2005 | Bischoff ...................... 700/248 |
| 2006/0142657 | A1 | 6/2006 | Quaid et al. |
| 2008/0161829 | A1 * | 7/2008 | Kang ........................... 606/130 |
| 2009/0000626 | A1 | 1/2009 | Quaid et al. |
| 2009/0000627 | A1 | 1/2009 | Quaid et al. |
| 2009/0012531 | A1 | 1/2009 | Quaid et al. |
| 2009/0012532 | A1 | 1/2009 | Quaid et al. |
| 2010/0192720 | A1 * | 8/2010 | Helmer et al. ............. 74/490.06 |

OTHER PUBLICATIONS

C. Plaskos 'Modeling and Design of Robotized Tools and Milling Techniques for Total Knee Arthroplasty.' PhD Thesis, Université Joseph Fourier, Grenoble, France, 2005.

* cited by examiner

Fig 5
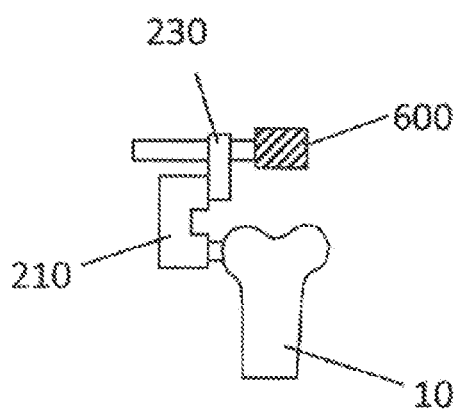
A
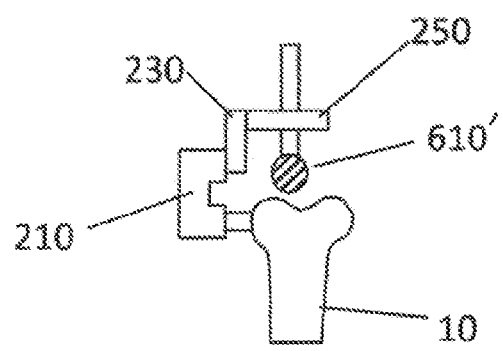
B

DYNAMIC PHYSICAL CONSTRAINT FOR HARD SURFACE EMULATION

CROSS-REFERENCE TO RELATED APPLICATIONS

The present application claims the benefit of U.S. patent application Ser. No. 61/064,486 filed Mar. 7, 2008, which is hereby incorporated by reference in its entirety.

TECHNICAL FIELD

The present invention relates to the field of haptic hard surface emulation and in particular, to an improved haptic method and system for emulating a hard surface which overcomes the disadvantages associated with conventional methods and systems and can advantageously be applied in a number of different applications, including surgical procedures.

BACKGROUND

Hard surface emulation is the ability of a manipulator to simulate a rigid virtual surface of relatively arbitrary shape. The use of such a surface implies projecting a virtual interface into a separate environment or workspace. As such, a user is able to move freely within this workspace until they come into contact with the interface. The most basic application of this concept is the use of a physical template, such as a ruler on a piece of paper.

Hard surface emulation in the context of assisting users to perform precision motion control tasks has a wide array of potential applications, ranging from large industrial part handling tasks to surgical procedures. Humans are not endowed with the high repeatability, precision or stability of robots. They are, however much better adapted to decision making and strategic planning in variable environments and in controlling physical interactions, such as those involved in using various tools. Haptic interfaces can be used to merge these distinct abilities.

To date, virtually all haptic research on stiff wall emulation has focused on impedance or admittance-generating algorithms. These algorithms are used to determine the forces or displacements required by the haptic architecture to emulate the virtual environment. Hard surfaces are typically approximated as a spring of given stiffness and hence require actual penetration of the virtual surface to activate the restoring forces. Due to hardware and software limitations, such as response lag time, joint backlash, structural flex, sensor noise, etc, systems based on this concept are not capable of rendering truly hard surfaces or of handling large or sustained user forces without causing instability or lack of precision. These requirements are, however, essential if one wishes to use haptic force feedback in guidance and region-restriction tasks.

A number of new concepts for emulating hard surfaces based both on modified control algorithms as well as on new mechanical concepts have been developed in order to resolve these challenges. One such concept is described in US patent application publication No. 2004/0128026A1, which is hereby incorporated by reference in its entirety. It has been applied in the form of a haptic robot, named Acrobot, and used in cutting tool guidance during total and unicompartmental knee arthroplasties. The concept introduces a region of increasing robot stiffness at the boundary of the free-motion and restricted regions. Within this region, the robot impedance increases and the admittance decreases based on the current location of the tool with respect to the restricted boundary. The purpose of Region II is to provide a smoother transition between the free motion region and the restricted region, thus preventing instability and decreasing the possibility of surface penetration due to delays in the control loop. The drawbacks are springiness at the boundary, vibrating motion at an inclined boundary and restricted motion along the boundary due to the increased impedance in this region. Some practical drawbacks are that a force transducer is required on the interface between the user and the device. Additionally, the structural architecture and motors must be able to provide sufficient impedance to the user, requiring large parts. This also creates significant friction in the system, requiring motion assistance from the robot to emulate uninhibited motion in the free region. All of this results in a relatively costly robot.

Another concept is described in U.S. Pat. No. 5,952,796, which is hereby incorporated by reference in its entirety, and is based on a continually variable transmission (CVT) concept. A CVT device is strictly defined as one having a continuous range of transmission ratios, independent of the amount of torque being applied to it. The drawbacks of this concept are that it necessarily requires force sensors to keep track of user intentions. Depending on the task, it can also result in rather bulky architectures with large amounts of inertia. More importantly, the inherent characteristic of the design in which the wheel steers continuously rather than in discrete steps, causes a sense of hesitation when the user rapidly pushes the device from rest and surface penetration when the device approaches a boundary at a high angle.

A third concept uses a double freewheel and motor combination that allows passive motion within a set of dynamic constraints, as described in U.S. Pat. No. 5,529,159, which is hereby incorporated by reference in its entirety. A freely rotating shaft is constrained by a freewheel to the rotational speed of a second parallel shaft driven by a motor. The concept allows the control of relative motion between two serial manipulator arms, each connected to one of the shafts. Two drawbacks with the design include low stiffness of the system and jagged motion in certain regions during path or surface following.

A fourth concept, called PTER and described in U.S. Pat. No. 5,704,253, which is hereby incorporated by reference in its entirety, is based on the use of clutches and brakes to regulate the relative rotational velocity between two manipulator links. The primary disadvantages of this system are penetration of the hard surface and smoothness during path-following tasks.

SUMMARY

The present invention provides a haptic method for emulating a hard surface including a hard, curvilinear surface. Unlike conventional methods, the present method provides a realistic feel of a hard surface to a user operating a manipulator. The present method can be used in any number of different applications. For example, the haptic method to emulate a hard surface according to one embodiment of the present invention can be used in surgery, such as but not limited to, robot-assisted surgery.

The present invention thus provides a means for hard surface emulation in haptic processes that creates a realistic feel in the virtual space for the user. It is another object of the invention to provide a means to prevent incursion within a virtual surface. The invention represents a improved haptic concept that aims to fulfill a number of objectives not readily met by presently available technologies. These objectives include but are not limited to: (1) realistic surface collision: collision with the virtual surface is as realistic as possible. Hence, minimal or no penetration of the surface occurs upon contact, regardless of the approach velocity and applied force; (2) realistic surface rigidity: a constant applied force by the user on the surface does not allow any detectable penetration of the surface or any motion of the surface (i.e. no springiness); (3) unimpeded surface departure: the action of pulling away from the surface does not result in any feeling of stickiness or impulse, regardless of the departure acceleration, initial velocity, or initial applied force; (4) smooth and precise surface tracing: intents by the user to trace the surface in any direction, result in unimpeded motion, as described in the next objective (no over- or under-penetration of the surface should occur, regardless of the speed of motion and applied force (i.e. no hysteresis or instability)); and (5) unimpeded motion freedom: when not in contact with the virtual surface, user motion is completely unimpeded with minimal apparent friction from the device. Gravity effects are situation-dependent and should be considered separately. Ideally, the haptic system is transparent to the user, as though it did not exist. By strictly adhering to this, gravity effects should not be compensated for, as is the case with any freely-held tool. However, depending on the situation, it may be useful to consider such compensation, where it may be necessary to prevent collapse of the system.

Several advantages of the present invention, in some of its forms, over existing methods and apparatus for the emulation of hard surfaces include but are not limited to: (1) provides the effect of a true collision with a hard surface; (2) does not necessarily require sensing of user's applied force; (3) allows smooth, unrestricted tracing of a virtual hard surface; (4) no stickiness when pulling away from a surface; (5) can successfully emulate planar, multi-planar and curvilinear surfaces; and (6) low-friction system with no backdriving of motors and gears.

In one embodiment, an apparatus for guiding the hand of a user includes a robot having an end-effector which is adapted to be manipulated by an application of external forces. The robot has at least one actuated joint and zero or more passive joints. The at least one actuated joint is configured to position a physical constraint that limits the motion of at least one other joint in at least one direction.

In another embodiment, a system for performing hard surface emulation in haptic processes includes a manipulator, such as a robot, that is adapted to be mounted to an object. The manipulator includes a first link that is movable about a first axis and a second link that is coupled to the first link and is movable about a second axis. The manipulator also includes an end-effector coupled to the second link and adaptable to be manipulated by an application of external forces. A physical constraint is provided and is selectively driven about the second axis to limit motion of the second link in at least one direction to control a user's movements relative to a virtual surface such that the end-effector is prevented from entering the virtual surface.

In another embodiment, a method for controlling a user's movements relative to a virtual surface includes the steps of: (a) applying a force on an end-effector of a manipulator causing motion at joints of the manipulator; (b) determining a current position of the end-effector; (c) comparing a position of the end-effector to a shape and location of the virtual surface; (d) determining a required position of a physical constraint in order to prevent incursion of the end-effector into the virtual surface; and (e) actively positioning the physical constraint to prevent the end-effector from entering into the surface.

These and other aspects, features and advantages of the present invention can be appreciated further from the description of certain embodiments and the accompanying drawing figures.

BRIEF DESCRIPTION OF THE DRAWING FIGURES

FIG. 5A is a side view of an exemplary configuration for peripheral bone milling;

FIG. 5B is a side view of an exemplary configuration for top-milling of a bone;

DETAILED DESCRIPTION OF EXEMPLARY EMBODIMENTS

Figure 1:
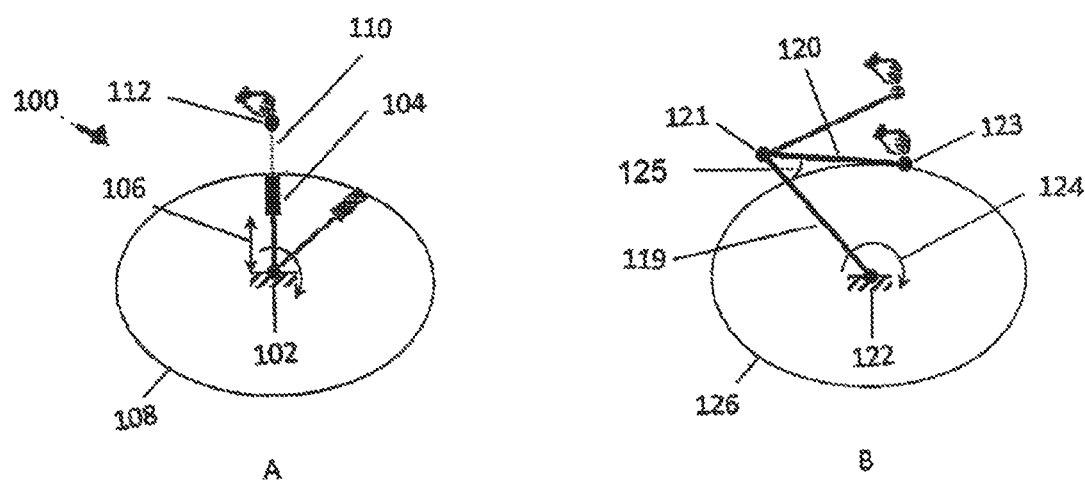
FIGS. 1A and 1B are perspective views illustrating general concepts of certain elements of the present invention.

A haptic method for emulating a hard surface according to at least one embodiment of the present invention has wide scale applicability to a number of different fields and it will be appreciated that the method can, therefore be used, for one, to provide directional guidance to a human user. Examples of such applications, that show the broad nature of the present invention, include, and are not limited to, the installation of automobile doors on an assembly line, needle guidance during pericardial puncture procedures to precisely guide a needle along a predetermined trajectory or drill guidance in pedicle screw placement in the spine.

Similarly, the method of the present invention can also be used to limit the user's motion to a virtual three-dimensional region. The system, therefore, allows the user to move freely within the region until he or she comes in contact with the boundaries. Some illustrational examples include: the avoidance of collisions when a human is handling fragile parts within a constrained environment, the prevention of a surgical tool from damaging soft tissue surrounding the operating environment, or a haptic device for bone sculpting used to provide cutting precision in a manner analogous to using a physical template, while still allowing the surgeon freedom of motion along the surface of the cut.

The present invention thus provides an apparatus and method for the emulation of a hard surface boundary in virtual space to replicate a physical space. The invention uses a dynamic physical constraint as a moving physical template that adjusts its position depending on the user's position in space. The invention provides a means for the replication of a hard surface boundary, and to prevent penetration of this surface, in virtual space, in order to recreate a physical space. The invention is applicable in haptic processes. In particular, the invention is applicable to haptic processes for surgery. The invention is especially applicable in bone sculpting surgery, including joint resurfacing arthroplasty surgery, such as knee or hip resurfacing. The present invention provides an apparatus and method for hard surface emulation by use of a physical constraint to limit the motion of a manipulator joint, where the position of the physical constraint is automated and controlled, and the position of the physical constraint is based on the location of the manipulator's end effector. The method and apparatus allow for the mechanisms which generate the dynamic physical constraints to be mechanically decoupled from the mechanisms that provide the passive guidance.

In yet another aspect, the present invention uses a physical constraint to limit the amount of motion of a manipulator joint. These manipulator joints may be of a variety of types, including, but not limited to, revolute (R) and/or prismatic (P). The position of the physical constraint can be controlled and automated using a computer. The positioning of the physical constraint at any given time is based on the location of the manipulator's end effector at that time. The present invention also allows for the mechanical decoupling of the mechanisms which generate the dynamic constraints from those that provide the passive guidance.

As previously mentioned, the present invention has application in a very wide array of uses. Such uses include, but are not limited to: any passive, semi-active or active manipulator or robot that requires joint constraints of the form of true hard collisions; the replacement of existing haptic joints so as to provide hard constraints; and the superposition over existing haptic joints to provide hard constraints. Further examples include a haptic manipulator used to constrain motion within a specified region; a haptic manipulator used to cast a virtual solid template into a working environment so as to improve motion precision; and superposition on existing haptic force-feedback joints to apply a final, hard limit.

FIG. 1(A) illustrates a simple form of a physical restraint concept in order to assist the reader in understanding the present invention. FIG. 1(A) is an example of a two-dimensional semi-active manipulator 100 having a rotational joint 102 at a base and a parallel prismatic joint 104 at an arm (RP configuration). The prismatic joint 104 is an active joint wherein its position along a direction 106 is controlled by an actuator (not shown). A second passive linkage (link) 110 has an end-effector 112 at the end of the link 110 which is intended to be the interface with the user (ie the part the user holds onto). The passive link 110 slides along the same direction as the active prismatic joint 104. At some point in the course of motion of the passive link 110, the passive link 110 physically collides with the active link 104 and cannot slide any further (i.e., it is 'blocked'). Both the active link 104 and passive link 110 rotate together about the rotational joint 102.

Given any convex virtual surface shape, the prismatic joint 104 adjusts its length radially (in direction 106), based on the manipulator's rotational position about the centre, to ensure the end effector is always on the surface 108. In this case, the manipulator is semi-active since the rotational degree of freedom 102 is passive, while the translational degree of freedom 104 is active.

In order to control the position of the user along the surface 108, the rotational degree of freedom may also be 'blocked' in a similar manner to how the passive linear link 104 is blocked, by using an angular restraint.

Another example of a two-dimensional implementation of the physical constraint concept is shown in FIG. 1B. Once again, a first joint 122 is revolute about a fixed centre point. A second joint 121 is also revolute, resulting in a common two-link rotational manipulator (RR configuration). The user holds on to an end-effector 123. The dynamic physical constraint, in this case, is applied at the manipulator's elbow, allowing free rotation of link 120 away from it, but obstructing motion towards it at a given angle 125. In other words, the user can apply scissor-like motion to the manipulator until contact with the angular (physical) constraint is achieved. This configuration is semi-active because all degrees of freedom are passive, while the revolute physical constraint actively adjusts itself depending on the current position of link 119 in order to prevent incursion into the surface 126. A particular advantage of this configuration is that a rotational constraint is very easily implemented using an electric motor. Its workspace is also large and adjustable.

The above described configurations are by no means exhaustive. PP, PR, and three or more degree of freedom configurations are possible. The invention relates to the dynamic physical constraint method of joint motion control. It should be noted that the architecture of the manipulator is situation-dependent, and the invention can thus be applied to numerous architectures for various applications. Multiple dynamic physical constraints can be used within the same device or system. A plurality of dynamic physical constraints could be used to provide joint constraint in multiple directions.

An aspect of the present invention is the use of a physical constraint that has its position dynamically controlled in order to create a physical barrier to motion of a manipulator in certain directions such that a predetermined curvilinear surface is emulated. The position of the dynamic physical constraint at any given time is determined by the position of the manipulator and/or end effector at that time. The position of the manipulator and/or end effector can be monitored by various means that perform the intended function. The steps of sensing the location of the manipulator and/or end effector, determining the correct position of the dynamic physical constraint, and controlling the movement of the dynamic physical constraint to the desired position can each be automated and controlled using various means, including the use of a computer(s).

In one embodiment, the apparatus and method of the present invention are particularly suited for application to robot-assisted surgery procedures, including, but not limited to, bone sculpting. Bone sculpting is the surgical procedure of shaping bone surfaces in preparation for the placement of orthopaedic implants. The typical tools used in such a procedure are an oscillating saw or a mill. The benefit of the former is its ability to do rapid planar cuts, and that of the latter is to do more complex cuts. The vast majority of commercial implants have a bone-mating surface whose profile is based on a single standard geometric shape, or a set of these shapes. A current trend in surgery, however, is placing increased importance on bone-conserving implants with more complex, anatomically similar bone-mating surfaces that require new tools capable of sculpting curvilinear surfaces in bone. Bone sculpting is a broad topic in orthopaedic surgery and finds its use in many procedures. Hip and knee arthroplasty are of primary importance because of their frequency.

Figure 2:
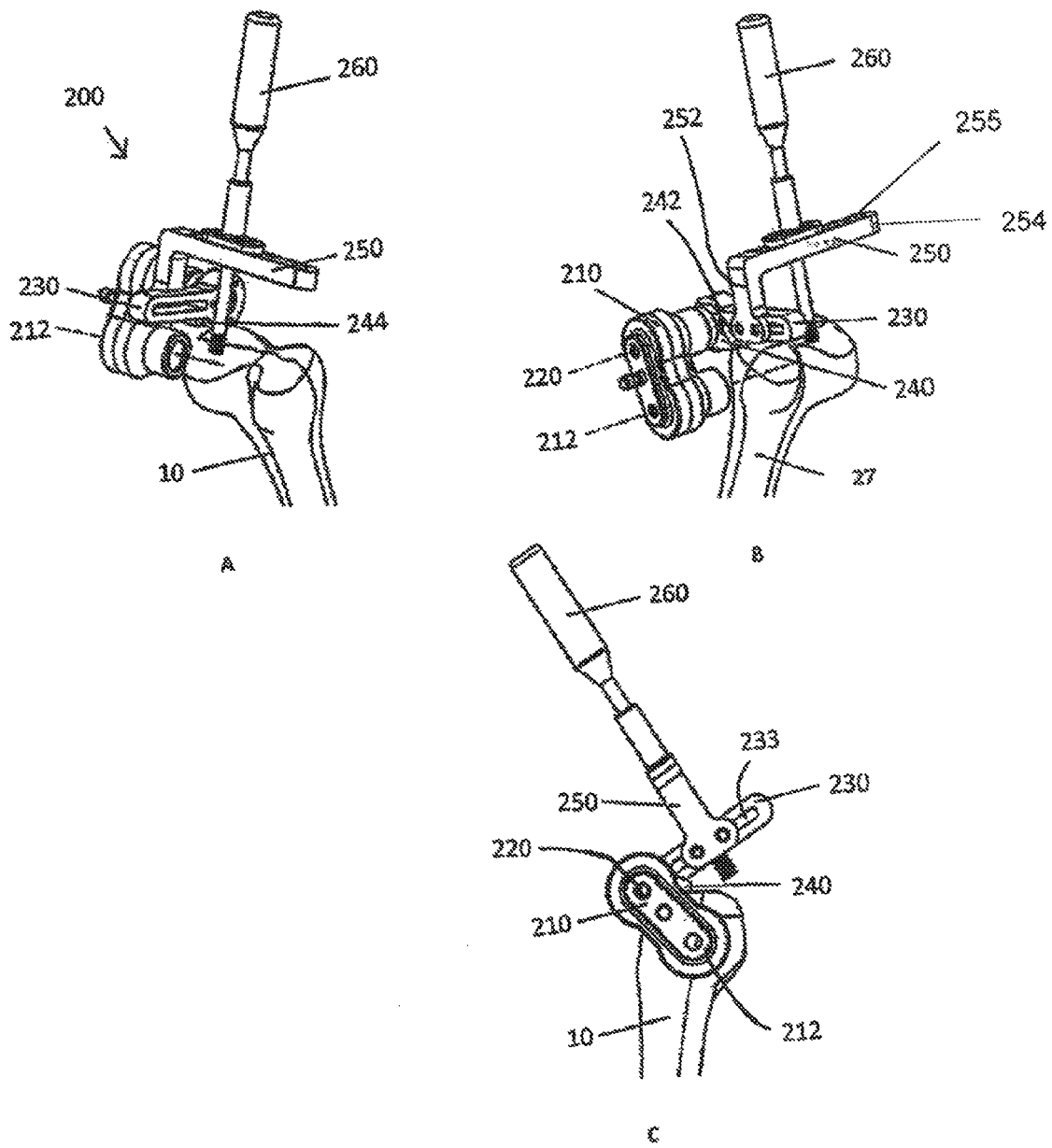
FIG. 2A is a perspective view of one embodiment of the present invention.
FIG. 2B is another perspective view of the embodiment of FIG. 2A.
FIG. 2C is a side view of embodiment of FIG. 2A.

An example of one architecture amongst many, which could be used for a semi-active femoral bone-mounted sculpting apparatus (tool) 200 is shown in FIGS. 2A-C. The apparatus 200 consists of a two-link RR manipulator and, as described with reference to FIG. 1B, the apparatus 200 is rigidly fixed to the lateral side of a femur bone 10. Fixation to the femur 10 can be done in a variety of methods, including those described in the following references, which are hereby incorporated by reference in their entireties: 1) PCT patent application publication No. WO2006106419, entitled Robotic guide assembly for use in computer-aided surgery; and 2) C. Plaskos 'Modeling and Design of Robotized Tools and Milling Techniques for Total Knee Arthroplasty.' PhD Thesis, Université Joseph Fourier, Grenoble, France, 2005.

The apparatus 200 includes a number of components that are constructed and configured to be coupled to and engage one another to permit controlled and precise sculpting of the femur 10. The apparatus 200 includes a first link 210 that can rotate freely about a first axis 212, and is equipped with a first sensor 500 (FIG. 6) to track its angular position about the first axis 212. A motor unit (not shown) is intended to be attached at a second axis 220 to provide controlled movement to the apparatus 200 as described in detail below. The illustrated first link 210 is an elongated structure with the first axis 212 being located proximate one end of the first link 210 and the second axis 220 being located proximate the opposite end of the first link 210. The position sensors disclosed herein can be any number of suitable conventional sensors, e.g., a Hall sensor. Similarly, any number of different motor units can be used in the present invention as described in the incorporated material. For example, the motor unit can be a brushless DC servomotor (Faulhaber BL 2036B).

Figure 3:
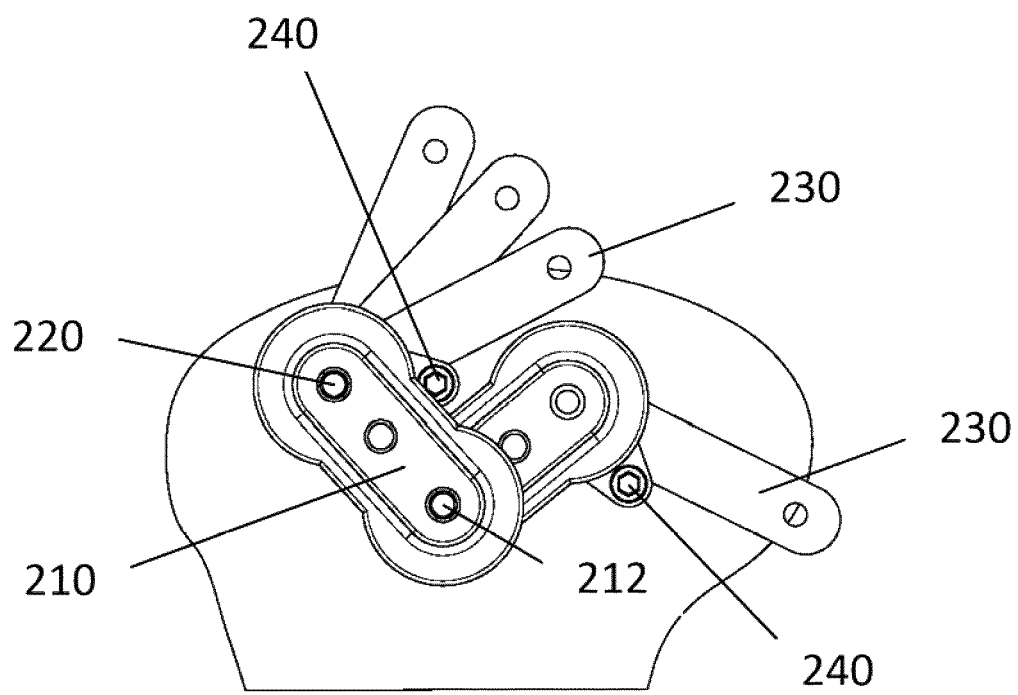
FIG. 3 is a side view showing different possible positions of the embodiment of FIG. 2A throughout a range of motion.

The apparatus 200 also includes a second link 230 that can rotate freely about the second axis 220, as shown in FIG. 3, until it comes in contact with a physical constraint 240 which is actively driven about the second axis 220 by the motor unit. In one embodiment, the second link 230 is an elongated structure that is coupled to the first link 210 at or proximate one end thereof and along the second axis 220. The physical constraint 240 can take any number of different forms so long as it operatively coupled to the motor unit and includes a portion that creates an interference or obstruction with the second link 230 when the two are in contact with one another. For example, in the illustrated embodiment, the physical constraint 240 includes a base 242 that is disposed about and rotatable about the second axis 220 and includes a protruding portion 244 (e.g., a pin) that represents the portion of the constraint 240 that is selectively placed in contact with the second link 230. The protruding portion 244 extends in a direction away from the first link 210.

An extension 250 to the second link 230 allows for the positioning of a bone mill 260 in the sagittal and coronal planes. Similar to the links, the extension 250 can be in the form of an elongated structure that is coupled to the second link 230 and includes a slot 255 formed therein. As shown, the extension 250 can have an L-shape in that a first leg 252 is coupled to the second link 230 and a second leg 254 represents the portion that receives the bone mill 260. The bone mill 260 extends through the slot 255 and can be moved longitudinally along the second leg 254 by moving within the slot 255. The first leg 252 can be coupled to the second link 230 by being coupled to a slot 233 that is formed in the second link 230, thereby permitting the extension 250 to be coupled to the second link 230 at different locations along the length of the second link 230 due to the ability of the extension 250 to move longitudinally within the slot 233.

The physical constraint 240 can be a backdrivable or a non-backdrivable positionable constraint. A non-backdrivable or non-reversible constraint 240 can be achieved by, for example, using a non-backdrivable gear such as a worm and worm-wheel gear coupled to the motor unit, and integrated into the motor unit. These gears absorb the forces at the output shaft using friction between their teeth, and not by the motor itself. Therefore, a relatively small and low power motor can be used.

Figure 4:
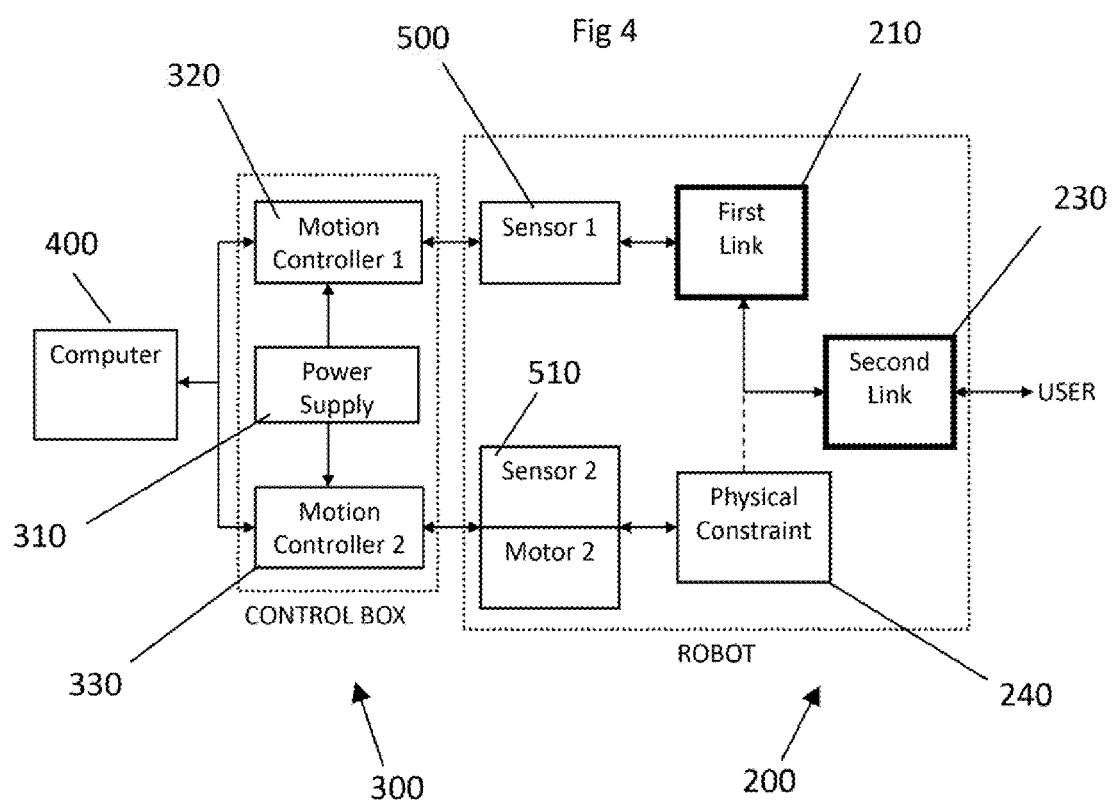
FIG. 4 shows an exemplary control scheme for controlling the embodiment of FIG. 2A.

A control box 300, illustrated by the block diagram in FIG. 4, consists of a power supply 310 and two motion controllers 320, 330 connected in series (one for each axis). In particular, the first motion controller 320 is for the first axis 212 and the second motion controller 330 is for the second axis 220. It will be appreciated that the first and second motion controllers 320, 330 communicate with a computer 400 through a communication port, generally shown at 402, and control the motor and sensor. The motion controllers 320, 330 can be any number of different motion controllers that are suitable for use in the intended applications described herein and others.

The user moves the bone mill 260 (end effector) located on the second link 230. The second link 230, in turn, interacts with the first link 210 continuously and with the physical constraint 240 only when the second link 230 and the physical constraint 240 are in contact. During these interactions, a first sensor 500 tracks the position of the first link 210 about the first axis 212 and sends the information continuously through the first motion controller 320 to the computer 400. The computer 400 then uses this information to decide where the physical constraint 240 should be positioned and sends this through the second motion controller 330 to the motor. When the second link 230 is not in contact with the physical constraint 240, the two robot links 210, 230 act passively and independently from the active part of the system 200. The active part of the system 200 includes the computer 400, the two motion controllers, the motor, the sensors and the dynamic physical constraint. A second sensor 510 tracks the position of the physical constraint 240 about the second axis 220.

In an alternative configuration, the motion controllers 320, 330 can be directly integrated into the motor unit, requiring only a short cable connection between the first and second motion controllers 320, 330 and the motors. This simplifies the cable connection between the robot (apparatus 200) and control box 300 allowing a cable with fewer wires to be used, and reduces the susceptibility of the system to interference and noise arising in the sensor signals.

Two distinct milling configurations are considered for purposes of illustration, and are graphically represented in FIGS. 5A and 5B. FIG. 5A shows a peripheral milling configuration in which a cylindrical milling bit 600 is oriented normal to the sagittal plane. FIG. 5B shows a top-milling configuration in which a ball-mill 610' is oriented in the sagittal plane. The former has the advantage of allowing a cylindrical surface to be cut in a single pass. Unless a shaped cutter is used, it is, however, limited to two-dimensionally varying surfaces. Since access is from the side, the peripheral milling configuration is less invasive than the top-milling configuration which requires full bone exposure from the top. The Major advantage of the top-milling configuration is that it allows for multi-pass contoured cutting of three-dimensionally varying surfaces. It also decreases the interference of the robot architecture with the surgeon's milling motions, since the mill is further away from the robot architecture.

Figure 6:
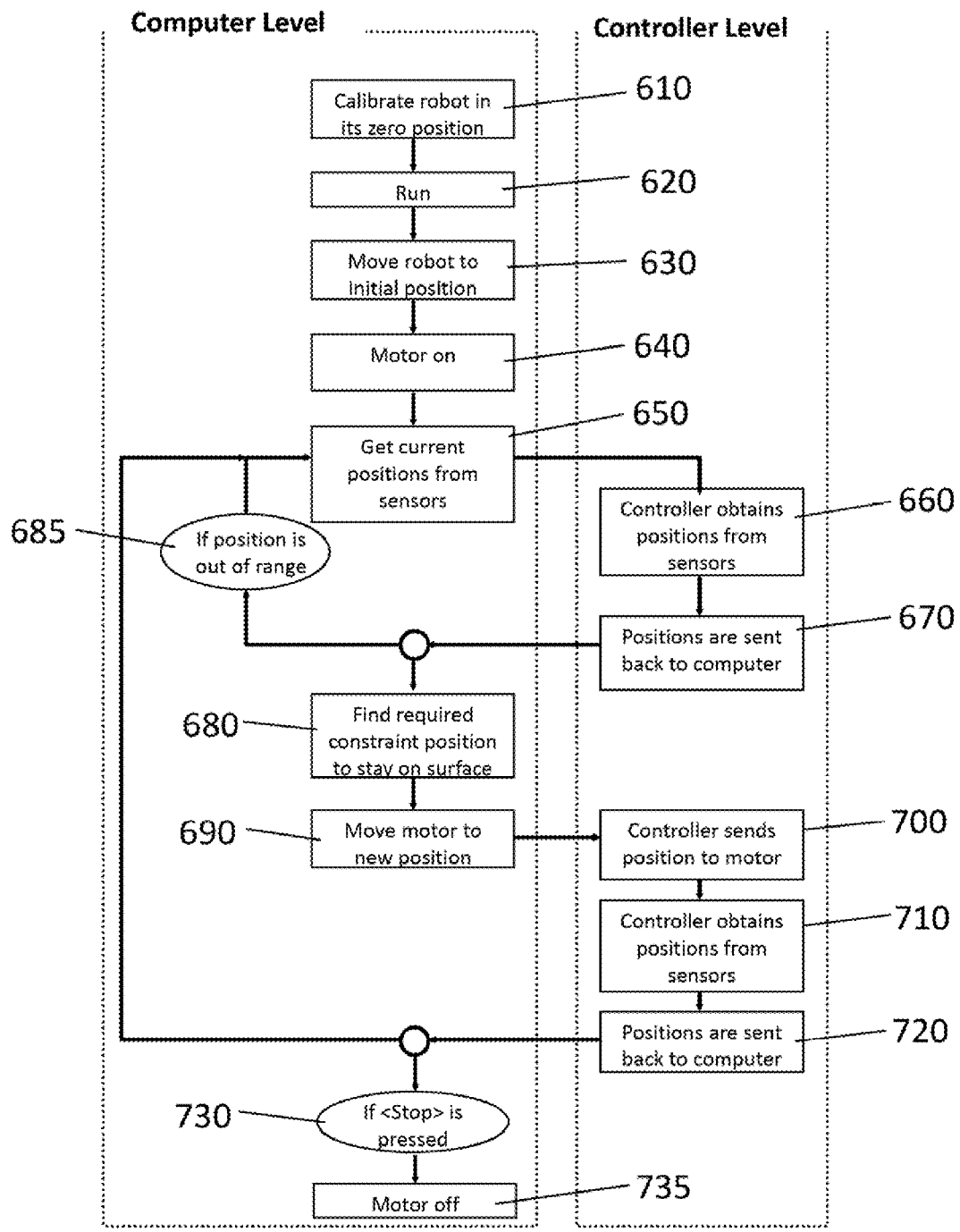
FIG. 6 shows an exemplary control program block diagram for the embodiment of FIG. 2A.

The active part of the system 200 is controlled by the computer 400. FIG. 6 shows a sample block diagram of a control program that can be used to control the active components of the apparatus 200 of the present invention. The control program relies on continuous readings of the position of the first axis 212. Based on this position, the program determines the respective position in which the physical constraint 240 must be placed to prevent incursion of the end effector into the virtual surface. This is done using a modified inverse kinematics calculation where the known variables are the position of the first joint, the equation of the virtual surface and the length of the robot links (e.g., links 210, 230), and the unknowns are the position of the second joint and the end effector. The actual implementation of these calculations can be done in various ways. Two possible ways include: A) the modified inverse kinematics can be calculated online using numerical methods to solve the non-linear problem, or B) basic inverse kinematics can be used beforehand to create a lookup table of the two link positions spanning the entire surface. The latter method then uses a generic binary search algorithm and interpolation to find the matching physical constraint position. Forward kinematics is computation of the position and orientation of robot's end effector as a function of its joint angles. It is widely used in robotics, computer games, and animation. The reverse process is known as inverse kinematics (i.e. the process of determining the jointed angles of a robot (or a kinematic chain) in order to achieve the desired pose). Inverse kinematics is a type of motion planning. Further details about these solutions to inverse kinematics can be found in 'HAPTIC EMULATION OF HARD SURFACES WITH APPLICATIONS TO ORTHOPAEDIC SURGERY' UBC Master's thesis, March 2008, by Nikolai Hungr, which is hereby incorporated by reference in its entirety.

The exemplary control method of FIG. 6 is now described in more detail. First, at a step 610, the robot (apparatus 200) is calibrated in its zero position. The program is run at step 620. The robot 200 is moved to an initial position in step 630 and in step 640, the motor is actuated. At step 650, the current positions of the first link 210 and the physical constraint 240 are obtained from the first and second sensors 500, 510. At step 660, the controllers 320, 330 obtain the positions from the first and second sensors 500, 510 and these positions are communicated back to the computer 400 at step 670. At step 680, the computer 400 determines the required position of the physical constraint 240 to stay on the surface. If it is determined that the position is out of range at step 685, then the program loops back to step 650. After the required position is determined at step 680, the motor is moved to a new position at step 690. At step 700, the controller sends the position to the motor and at step 710, the controller obtains the positions from the sensors 500, 510. At step 720, the positions are sent back to the computer 400. The process continues to loop back to the step 650; however, at step 730, if a stop button or the like is pressed, then the motor is turned off at step 735.

Figure 7:
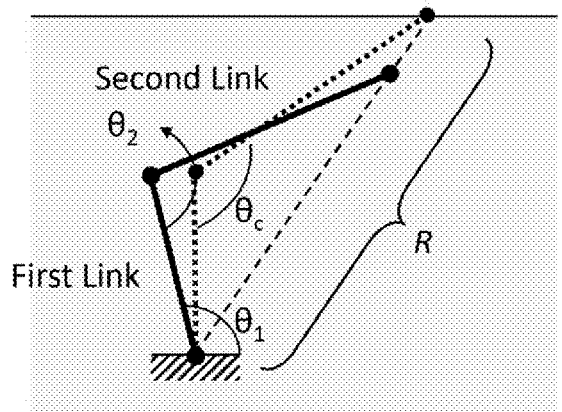
FIG. 7 illustrates an additional method of determining the required physical constraint location for the embodiment of FIG. 2A.

Another control method can be seen in FIG. 7. As opposed to the previously described control method of FIG. 6, the computer 400 reads the current position of both joints. Applying forward kinematics, the current position of the end effector (whether in contact with the virtual surface or not) can be calculated online. Then, using geometry, the radial distance R between the robot base and the virtual surface can be calculated and used to determine the physical constraint's required position to prevent penetration into the surface. Alternatively, the closest position on the surface to the current end-effector position can be calculated. The current direction of the end-effector velocity could also be used to predict the required position of the physical constraint as it approaches the surface.

Figure 8:
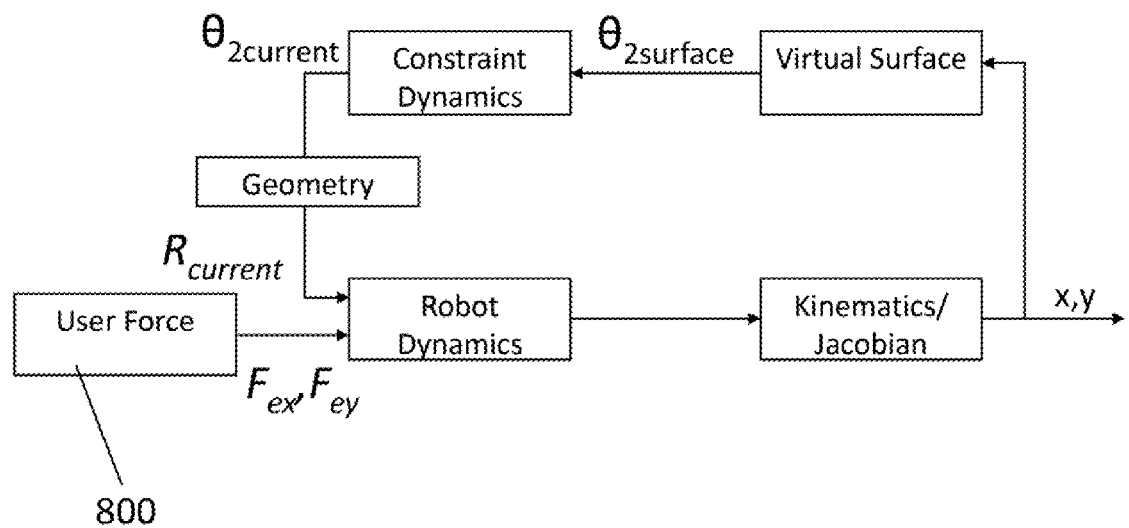
FIG. 8 shows an exemplary control scheme block diagram for a manipulator based on one embodiment of the present invention.

These control methods can be summarized by the block diagram shown in FIG. 8. At step 800, the user applies a force on the end-effector (e.g., bone mill 260). These forces act on the robot 200 causing motion at the joints (between the parts (links) of the robot 200). The kinematics of the manipulator allow one to determine the current position of the end-effector which is compared to the shape and location of the virtual surface. The required position of the physical constraint 240 in order to prevent incursion into the surface is determined and applied to the robot 200, affecting the robot dynamics and hence closing the loop.

An additional embodiment of this invention would be the extension of the dynamic physical constraint concept shown in FIGS. 2A-C to three or more degrees of freedom. For example, a linear encoder could be placed on the slot 255 in the extension piece 250. This would be used to track the location of the mill 260 in the medio-lateral direction. The three-dimensional milling surface could be modeled by a set of planar contours in the sagittal plane. Depending on the medio-lateral location of the mill 260, the physical constraint 240 would be positioned to the appropriate contour.

Figure 9:
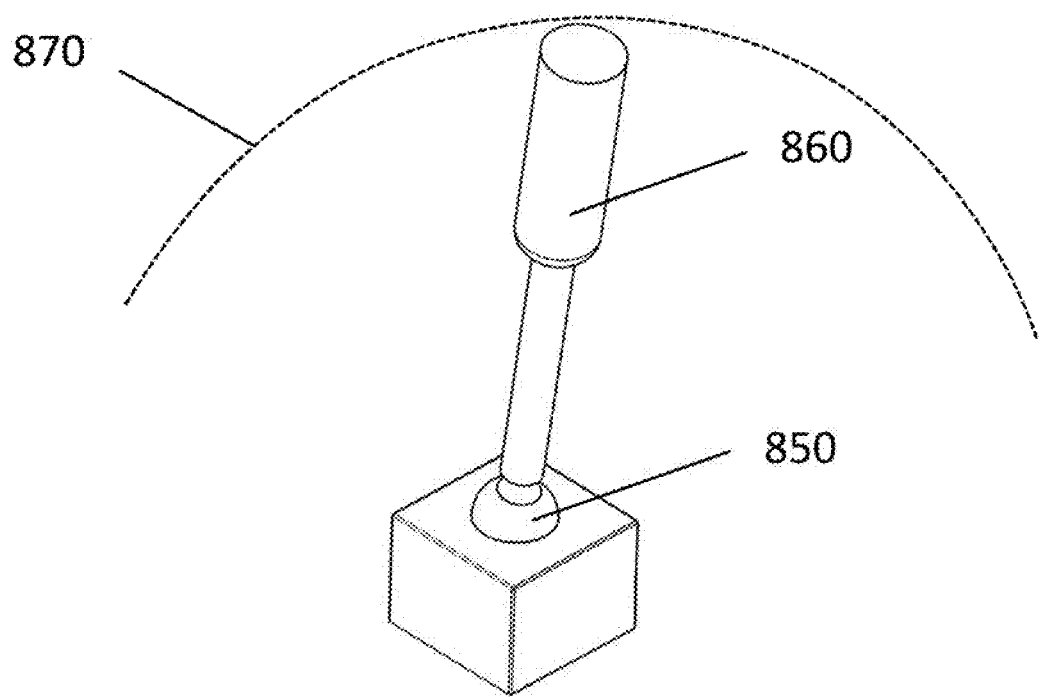
FIG. 9 shows an additional embodiment of the present invention based on a piston-cylinder configuration.

An additional embodiment includes an architecture based on a ball joint (or double revolute joint) and a linear physical constraint or piston-cylinder arrangement (RRP configuration), as illustrated in FIG. 9. In such a system, a ball joint 850 would be freely mobile and its position would be monitored. Based on this position, the linear physical constraint 860 would adjust its radial length preventing incursion into the virtual surface 870. This could be applied for 2D as well as 3D surfaces.

In another embodiment of the present invention, one or more of the passive links can be configured so that they can be actively controlled by an actuator, motor or the like. This would allow an additional level of control in regions inside the workspace of the manipulator, and could be used for a variety of purposes (for example, for providing gravity compensation or variable stiffness near the boundaries of the virtual surface). Any known control strategy can be used, including impedance control.

The application of the dynamic physical constraint concept of the present invention is very broad. The design provides a realistic feeling of a hard surface. The invention provides a true sense of touch through a manipulator. The concept could be used in the design of haptic interfaces in a large variety of applications, and in a large variety of fields. Some examples include robot-assisted surgery procedures, desktop virtual environments (such as a three dimensional spatial mouse or joystick), industrial applications, and telemanipulation tasks. Other examples include use to prevent collision of a manipulator with other parts in a constricted industrial environment, such as in manufacturing processes.

More specifically in the surgical field, the invention could also be used for a large variety of applications other than that stated in the preferred embodiment. For example, it could be used for implant-bone surface preparation in joints other than the knee, including for example hip, elbow, and ankle joints. It could also be used in osteotomies, in general, wherever there is a need for accurate curvilinear bone milling. An example is a Ganz osteotomy, in which the acetabulum is deepened to restore the patient's anatomical alignment.

Depending on the intended use of the invention, certain parameters of various embodiments can be adjusted and/or controlled as necessary to provide an optimal response. Such parameters include, but are not limited to: the response time of the controlling mechanism, the attachment point of an axis of the robot with respect to the surface being emulated, the length(s) of the link(s), the motor and sensor sizes, etc.

Furthermore, the invention could be incorporated in a computer-assisted orthopaedic surgery (CAOS) system, such as the one described in the abovementioned patent WO2006106419, or any other commercially available system. These systems typically use 3D position measuring localizers to track the positions of bones and tools in space. Such a positioning measurement system could be used to track the position of the milling tool during bone sculpting, and if precise enough, could replace the sensor used to track the orientation of the passive link or links.

Although the present invention has been described as a method and apparatus for haptic hard surface emulation, it should be noted that the system is very flexible and could also be used to emulate non-rigid, soft or springy surfaces. This can be accomplished by adjusting the stiffness and motor torque parameters of the active system accordingly, as is normally done in haptic robotics and previously described in the abovementioned patent application US 2004/0128026A1. The present invention is therefore a very flexible and useful one as it can more realistically emulate hard surfaces while still being capable of emulating soft ones.

It will be appreciated that the dynamic physical constraint 240 can be used to emulate a variety of virtual surfaces. For example, an ellipse is an example of relatively simple surface requiring minimal motion of the dynamic physical constraint 240 along the length of the surface. A horizontal line is a more complex example as it requires more motion of the dynamic physical constraint as the extremities of the line are approached. A hybrid circle/ellipse surface is a modified version of the ellipse and has a tighter radius of curvature. A sine wave is a much more complex surface, as the wave sits on the already complex horizontal line. A tri-planar surface is a simplified version of the horizontal line that keeps the surface more convex about the center of the robot.

While the invention has been described in connection with a certain embodiment thereof, the invention is not limited to the described embodiments but rather is more broadly defined by the recitations in the claims below and equivalents thereof.

What is claimed is:

1. A system for performing hard surface emulation in haptic processes comprising:
    a manipulator that includes:
        a first link that rotates about a first axis;
        a second link coupled to the first link and independently rotatable about a second axis;
        an end-effector coupled to the second link and configured to be manipulated by an application of external forces; and
        a single physical constraint selectively driven and independently rotatable about the second axis to limit motion of the second link in only one direction to control movement of the end-effector relative to a predetermined position of the physical constraint.

2. The system of claim 1, wherein the manipulator is mounted to the object about the first axis.

3. The system of claim 1, wherein the system is a hone sculpting system and the end-effector is a tool for sculpting a bone to which the manipulator is mounted.

4. The system of claim 1, wherein the one direction comprises rotation about the second axis.

5. The system of claim 1, wherein the first link has a first sensor associated therewith that measures a position of the in link about the first axis and the physical constraint has a second sensor associated therewith that measures a position of the physical constraint, the system further including:
    a controller for controlling movement of the manipulator, the controller including
        (1) a power supply;
        (2) a first motion controller in communication with the first sensor; and
        (3) a second motion controller in communication with the second sensor and a motor that drives the physical constraint; and
    a computer in communication with the controller and configured to track the location of the first link via information received from the first sensor and track the location of the physical constraint via information received from the second sensor.

6. The system of claim 1, wherein a position of the physical constraint is dynamically controlled in order to create a physical barrier to motion of the end-effector.

7. The system of claim 5, wherein the computer executes a control program that receives continuous readings on a position of the first link and based on the position of the first link, the computer determines a respective position in which the physical constraint must be placed.

8. The system of claim 1, wherein the physical constraint comprises:
    a base portion rotatable about the second axis; and
    a protruding portion that extends from the base.

9. The system of claim 8, wherein the protruding portion is a pin that extends from the base in a direction away from the first link.

10. The system of claim 1, when the manipulator further comprises an extension member for slidably receiving the end-effector, the extension member extending from the second link in a direction parallel to the first axis.

11. The system of claim 10, wherein the extension member includes a slot extending through the extension member in a direction substantially perpendicular to the first axis.

12. The system of claim 1, wherein the second link further rotates about the first axis.

13. The system of claim 1, wherein the manipulator further comprises an extension member for slidably translating the end-effector.

14. A system for performing hard surface emulation in haptic processes comprising:
    manipulator that includes:
        a first link that rotates about a first axis;
        a second link independently slidable relative to the first link along a second axis;
        an end-effector coupled to the second link and configured to be manipulated h an application of external forces; and
        a single physical constraint selectively driven and independently slidable along the second axis to limit motion of the second link in only one direction to control movement of the end-effector relative to a predetermined position of the physical constraint.

15. The system of claim 14, wherein the manipulator further comprises an extension member slidably translating the end-effector.

* * * * *